US011123056B2

(12) United States Patent
Nowak et al.

(10) Patent No.: US 11,123,056 B2
(45) Date of Patent: Sep. 21, 2021

(54) RING RETRACTOR SYSTEM (71) Applicant: Thompson Surgical Instruments, Inc., Traverse City, MI (US)

(72) Inventors: Steve Nowak, Traverse City, MI (US); Travis Witulski, Traverse City, MI (US); Christopher T. Martin, Cedar, MI (US)

(73) Assignee: THOMPSON SURGICAL INSTRUMENTS, INC., Traverse City, MI (US)

( * ) Notice: Subject to any disclaimer, the term of this patent is extended or adjusted under 35 U.S.C. 154(b) by 82 days.

(21) Appl. No.: 16/420,595

(22) Filed: May 23, 2019

(65) Prior Publication Data
US 2020/0367875 A1 Nov. 26, 2020

(51) Int. Cl.
*A61B 17/02* (2006.01)
*A61B 17/00* (2006.01)

(52) U.S. Cl.
CPC ........ *A61B 17/0218* (2013.01); *A61B 2017/00367* (2013.01); *A61B 2017/00477* (2013.01)

(58) Field of Classification Search
CPC .......... A61B 17/06061; A61B 17/0206; A61B 17/025; A61B 17/02; A61B 17/1671; A61B 17/3423; A61B 17/7074; A61B 2017/00367; A61B 2017/00477; A61B 2017/0287; A61B 2017/2927; A61B 2017/0046; A61B 2017/00022; A61B 2017/2929; A61B 1/32; A61B 90/50; A61B 34/70
See application file for complete search history.

(56) References Cited

U.S. PATENT DOCUMENTS

| | | | |
|---|---|---|---|
| 2,586,488 A | 2/1952 | Smith | |
| 4,254,763 A | 3/1981 | McCready et al. | |
| 4,421,107 A | 12/1983 | Estes et al. | |
| 4,457,300 A | 7/1984 | Budde | |
| 4,510,926 A * | 4/1985 | Inaba | A61B 90/50 600/231 |
| 5,284,129 A | 2/1994 | Agbodoe et al. | |
| 5,902,233 A | 5/1999 | Farley et al. | |
| 6,659,945 B2 | 12/2003 | Ball et al. | |
| 7,052,454 B2 * | 5/2006 | Taylor | A61B 17/3423 600/114 |
| 8,231,528 B1 * | 7/2012 | Friedrich | A61B 17/02 600/228 |

(Continued)

*Primary Examiner* — Pedro Philogene
(74) *Attorney, Agent, or Firm* — McAndrews, Held & Malloy, Ltd.

(57) ABSTRACT

A retractor system can include a ring frame and a clamp. The ring frame can include a first ring segment and a second ring segment detachably joined to a first ring segment at a joint. The joint can be contained within a cross section of the ring frame that corresponds to a cutting plane perpendicular to an outer surface of the ring frame. The clamp can include an adjustment screw and a first set of jaws and a second set of jaws. The first set of jaws and second set of jaws can define a first aperture configured to receive the ring frame. Rotation of the adjustment screw in a tightening direction can cause the first set of jaws to engage the outer surface of the ring frame and apply a first clamping force to the outer surface of the ring frame received by the first aperture.

19 Claims, 9 Drawing Sheets

(56) References Cited

U.S. PATENT DOCUMENTS

| | | |
|---|---|---|
| 9,320,506 B2 * | 4/2016 | Bertagnoli ......... A61B 17/0206 |
| 9,872,675 B2 | 1/2018 | Nowak et al. |
| 10,238,375 B2 | 3/2019 | O'Connell et al. |

* cited by examiner

RING RETRACTOR SYSTEM

BACKGROUND

The present disclosure relates to retractor systems and retractors that are used to retract soft tissue and other anatomy of a patient.

During a surgical procedure, a surgeon can make an incision in a patient to access internal organs, bones, and/or other anatomical structures. Retractors can be used to hold back soft tissue and other patient anatomy in the immediate area of the incision. Such retractors can provide the surgeon with a view of the internal organs, bones, and/or other anatomical structures. Furthermore, the retractors can maintain an opening via which the surgeon can access the anatomical structures with one or more surgical tools.

The usefulness of any retractor device is limited by the number of ways that the retractor can be positioned with respect to the retracted anatomy as well as the ease with which the surgeon can adjust the relative position of the retractor both before and during surgery. The less obstructive, the less obtrusive, and the more versatile a retractor device, the more desirable it becomes for use in the above-described manner.

Further limitations and disadvantages of conventional and traditional approaches will become apparent to one of skill in the art, through comparison of such approaches with the present disclosure as set forth in the remainder of the present application with reference to the drawings.

SUMMARY

Various aspects of this disclosure are related to a retaining system that includes retractors used to retract anatomy in order to provide exposure of an operative site. For example and without limitation, various aspects of the disclosure are directed to a ring frame. The ring frame can be assembled from multiple ring segments. The ring frame can later disassembled for ease of storage, cleaning, etc. In particular, the ring segments can include joints that join the ring segments together without proximate protrusions. Retractors can be attached to the assembled ring frame using clamps that engage outer surfaces of the ring frame. The attached retractors can be repositioned along the ring by, for example, sliding clamps along the assembled ring frame while still engaged with the outer surfaces of the ring frame. Due to the lack of protrusions about the joints, the clamps can be slid across joints without detaching the clamps from the assembled ring. The ring segments and joints, in some embodiments, can provide the ring frame with a uniform diameter that permits securing a clamp to the ring frame anywhere along the ring frame including at a joint between ring segments. Thus, due to the lack of protrusions and uniform diameter, a surgeon can more readily adjust and position retractors with respect to an incision site without concern as to locations of joints along the ring frame.

DETAILED DESCRIPTION

Various aspects of the present disclosure can be embodied in many different forms and should not be construed as being limited to the example embodiments set forth herein. Rather, these example embodiments of the disclosure are provided so that this disclosure will be thorough and complete and will convey various aspects of the disclosure to those skilled in the art.

According to various embodiments of the present disclosure, a retractor system can include a ring frame and a clamp. The ring frame can include a first ring segment and a second ring segment detachably joined to a first ring segment at a joint. The joint can be contained within a radial cross section of the ring frame that corresponds to a cutting plane perpendicular to an outer surface of the ring frame. The clamp can include a first set of jaws. The first set of jaws can define a first aperture configured to receive the ring frame. The first set of jaws to engage the outer surface of the ring frame and apply a first clamping force to the outer surface of the ring frame received by the first aperture.

According to further embodiments of the present disclosure, a ring frame for a retractor system can include ring segments detachably joined to one another at a plurality of joints. The ring segments can provide an outer surface of the ring frame with a generally uniform cross section. Each joint can be contained within the generally uniform cross section.

According to yet other embodiments of the present disclosure, a clamp is provided for a retractor system comprising an elongated frame member. The clamp can include a segmented body and an adjustment screw. The segmented body can include a first segment, a second segment, and a bore through the first segment and the second segment. The first segment can include a first upper surface, a first lower surface, and a first side surface coupling the first upper surface to the first lower surface. The second segment can include a second upper surface, a second lower surface, and second side surface coupling the second upper surface to the second lower surface. The adjustment screw can pass through the first segment and the second segment via the bore. An upper jaw of the first segment and a lower jaw of the second segment can define a first aperture that passes through the first side surface of the first segment and the second side surface of the second segment. Rotation of the adjustment screw in a tightening direction can cause the first segment and the second segment to apply a first clamping force to an outer surface of the elongated frame member passing through the first aperture.

The following discussion presents various aspects of the present disclosure by providing examples thereof. Such examples are non-limiting, and thus the scope of various aspects of the present disclosure should not necessarily be limited by any particular characteristics of the provided examples. In the following discussion, the phrases "for example," "e.g.," and "exemplary" are non-limiting and are generally synonymous with "by way of example and not limitation," "for example and not limitation," and the like.

As utilized herein, "or" means any one or more of the items in the list joined by "or." As an example, "x or y" means any element of the three-element set $\{(x), (y), (x, y)\}$.

In other words, "x or y" means "one or both of x and y." As another example, "x, y, or z" means any element of the seven-element set {(x), (y), (z), (x, y), (x, z), (y, z), (x, y, z)}. In other words, "x, y, or z" means "one or more of x, y, and z."

The terminology used herein is for the purpose of describing particular examples only and is not intended to be limiting of the disclosure. As used herein, the singular forms are intended to include the plural forms as well, unless the context clearly indicates otherwise. It will be further understood that the terms "comprises," "includes," "comprising," "including," "has," "have," "having," and the like when used in this specification, specify the presence of stated features, integers, steps, operations, elements, and/or components, but do not preclude the presence or addition of one or more other features, integers, steps, operations, elements, components, and/or groups thereof.

It will be understood that, although the terms first, second, etc. can be used herein to describe various elements, these elements should not be limited by these terms. These terms are only used to distinguish one element from another element. Thus, for example, a first element, a first component, or a first section discussed below could be termed a second element, a second component, or a second section without departing from the teachings of the present disclosure. Similarly, various spatial terms, such as "upper," "lower," "side," and the like, can be used in distinguishing one element from another element in a relative manner. It should be understood, however, that components can be oriented in different manners, for example a device can be turned sideways so that its "top" surface is facing horizontally and its "side" surface is facing vertically, without departing from the teachings of the present disclosure.

In the drawings, various dimensions can be exaggerated for illustrative clarity. Additionally, like reference numbers are utilized to refer to like elements through the discussions of various examples.

The discussion will now refer to various example illustrations provided to enhance the understanding of the various aspects of the present disclosure. It should be understood that the scope of this disclosure is not limited by the specific characteristics of the examples provided and discussed herein.

Figure 1:
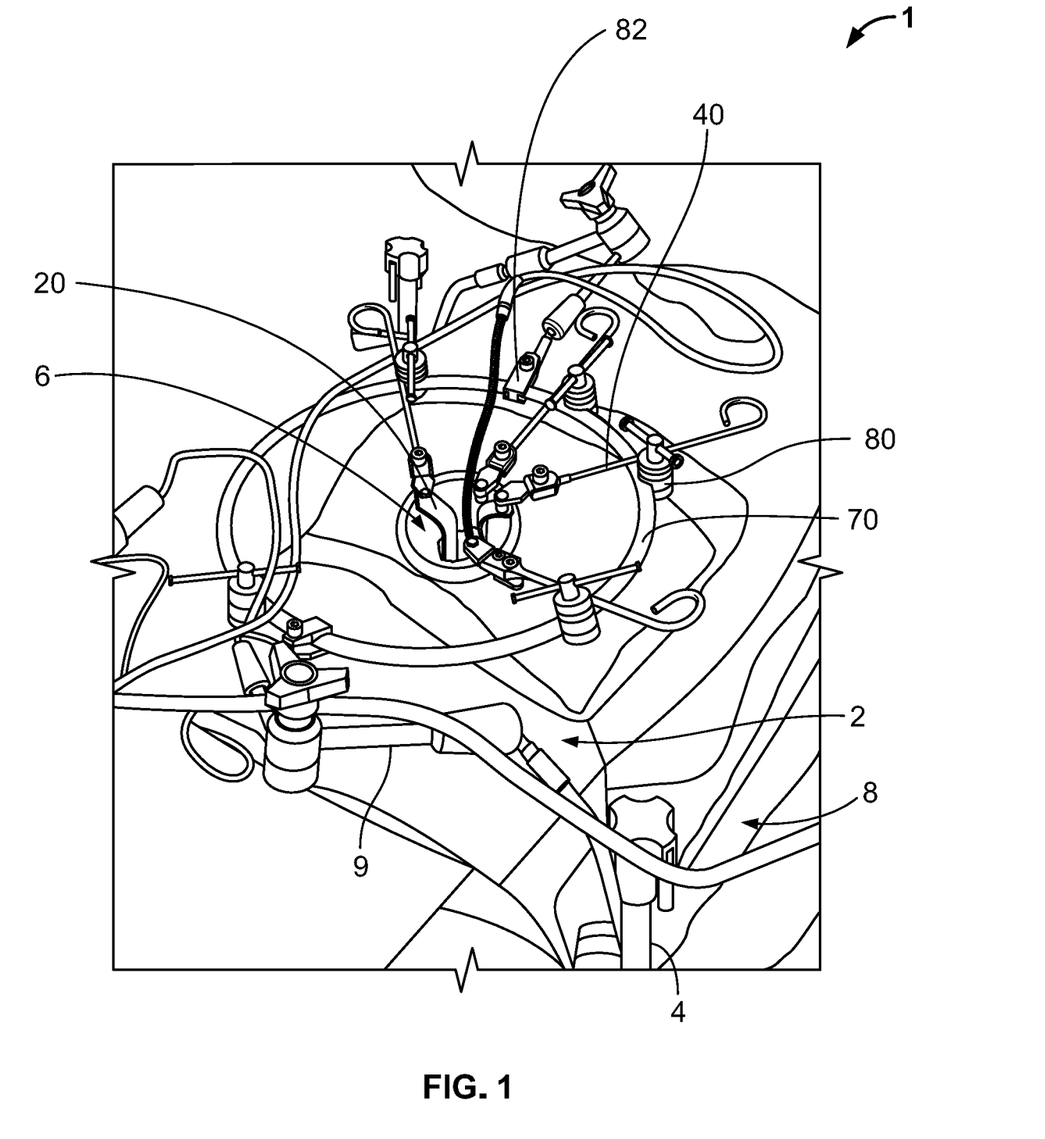
FIG. 1 provides a perspective view of an example embodiment of a retractor system used to retract soft tissue of a surgical site in accordance with various aspects of the present disclosure.

FIG. 1 illustrates an embodiment of a retractor system 1 in accordance with various aspects of the present disclosure. The retractor system 1 can include a frame assembly 2, a ring frame 70 secured to the frame assembly 2, and retractors 20 secured to the ring frame 70 via clamps 80 and retractor arms 40.

The frame assembly 2 can include one or more posts 4 and frame arms 9. Each post 4 can be fixed to a surgical table or bed 8 such that the post 4 extends upward in a generally vertical direction. Each post 4 can provide a location to which one or more frame arms 9 can be secured. In the illustrated embodiment, the frame arms 9 generally extend from the posts 4 and over table or bed 8.

As further shown, the ring frame 70 can be attached to the one or more frame arms 9 via clamps 82. Similarly, retractors 20 can be attached to the ring frame 70 via clamps 80. As shown, the frame arms 9 can position the attached ring frame 70 such that the ring frame 70 and attached retractors 20 generally circumscribe a surgical site 6.

Details regarding an embodiment of a screw-type clamp 80 are discussed below with respect to FIGS. 8-17. Clamps 82 of the retractor system 1 can be implemented in a similar manner. Moreover, while clamps 80, 82 can be implemented using screw-type clamps as shown in FIGS. 8-17, other types of clamps can also be used. For example, one or more of clamps 80, 82 can be implemented using a lever-type clamp similar to the clamps described in U.S. Pub. 2017/0042527, entitled "Surgical Retractor Having Clamping Mechanism," which is hereby incorporated by reference in its entirety.

Figure 2A:
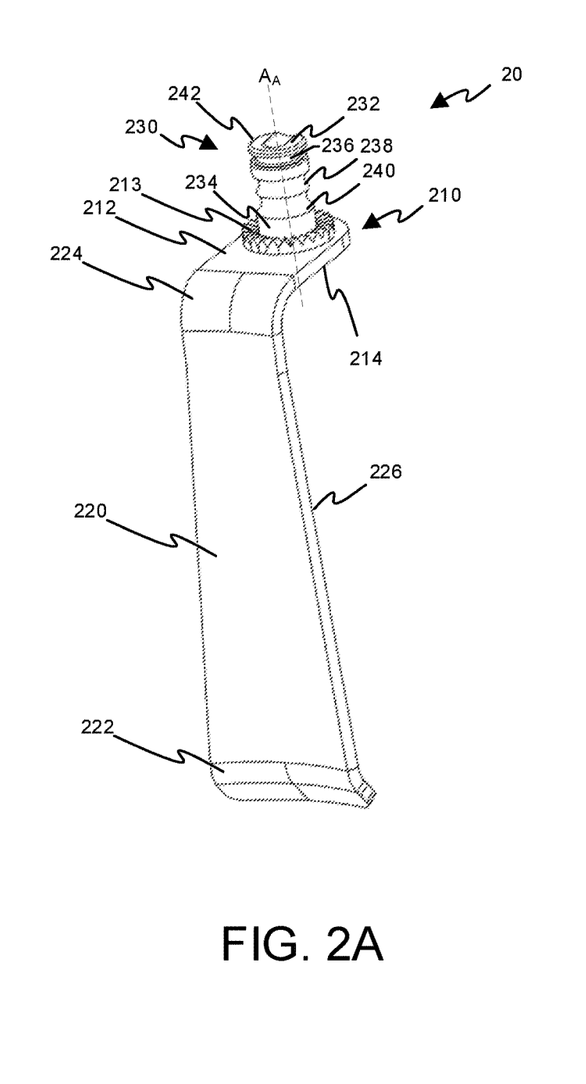
FIGS. 2A and 2B depict example retractors of the retractor system shown in FIG. 1.
Figure 2B:
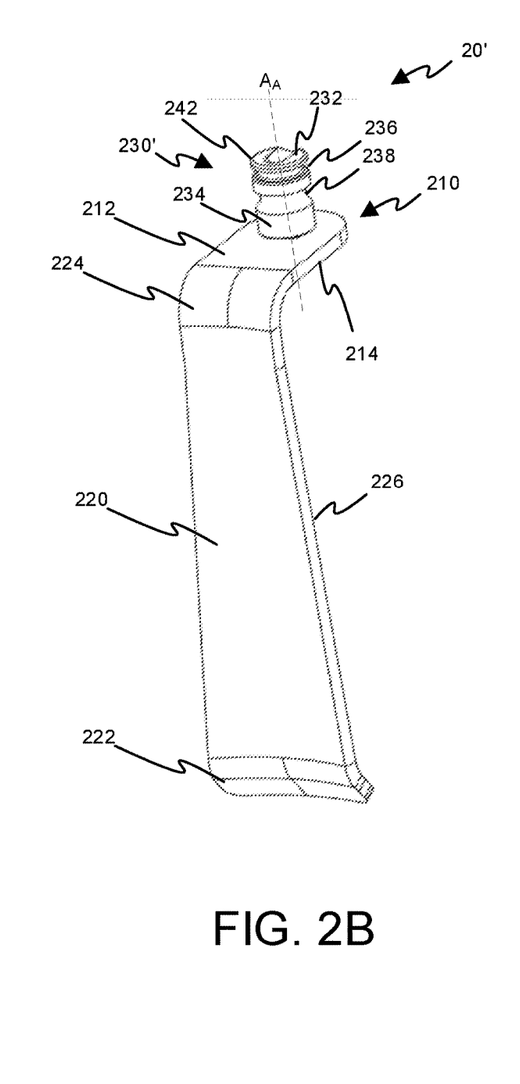

FIGS. 2A and 2B provide a perspective view of a first retractor 20 and a second retractor 20' representative of the retractors 20 of FIG. 1. In general, the retractors 20, 20' can include a retractor body 210 and one or more blades 220 extending therefrom. Each blade 220 can include a smooth, thin plate with dull edges that is inserted into an incision to pull back the tissue. The blades 220 can come in many different sizes depending on the particular application and physical characteristics of the patient. The blades 220 can be slightly curved or completely flat, and can have end prongs of various configurations to make it easier to pull back tissue.

As depicted, the blade 220 can comprise a distal end 222, a proximal end 224, and a retracting portion 226. The distal end 222 generally corresponds to the end of the blade 220 inserted into an incision of a patient during a surgical procedure, and the proximal end 224 generally corresponds to the end of the blade 220 extending from the incision and out of the patient during a surgical procedure.

The proximal end 224 can join the blade 220 to the retractor body 210, resulting in the retracting portion 226 generally extending or projecting from the retractor body 210 toward the distal end 222. As shown, the retracting portion 226 can form a 90° angle with the retractor body 210; however, other angles between the retracting portion 226 and the retractor body 210 are contemplated and can be more suitable for certain surgical procedures. The retracting portion 226 can be sized and adapted to hold back tissue from a site of interest during a procedure. In certain embodiments, the retractor system 1 can include a number of differently sized or shaped blades 220 to provide increased adaptability for different procedures or patients.

As noted above, the retractor body 210 can be attached to one or more blades 220. The retractor body 210 can include a generally planar upper surface 212 and a generally planer lower surface 214 that is coplanar with the upper surface 212. The retractor body 210 can further include an attachment post 230, 230'. In particular, the attachment post 230, 230' can extend upwardly from the upper surface 212 of the retractor body 21; whereas the blade 220 can extend downwardly from the upper surface 212 of the retractor body 210.

The attachment post 230, 230' can be sized and adapted for attachment to a connector 408 of a retractor arm 40. To this end, the attachment post 230, 230' can have a generally cylindrical-shape with a circular cross-section. The attachment post 230 can extend from the upper surface 212 of the retractor body 210. A longitudinal axis $A_A$ of the attachment post 230, 230' can extend at a right angle from the upper surface 212; however, the attachment post 230 in some embodiments can extend from the upper surface 212 at other angles.

The attachment post 230 can include a top surface 232 and a side surface 234. The side surface 234 can include upper, central, and lower groove 236, 238, 240. Each of the grooves 236, 238, 240 can be circumferential around the attachment post 230. The diameter of the attachment post 230 can be sized such that the attachment post 210 can pass through an attachment port 412 of the connector 408.

The central groove 238 and the lower groove 240 can be positioned along the side surface 234 to vertically align the attachment post 230 within the port 412. A locking ball 416, cam, or other member of the connector 408 can engage either the central groove 238 or the lower groove 240 to position the attachment post 230 longitudinally within the port 412. The side surface 234 and grooves 238, 240 can be tapered. Such tapering can aid or guide the locking ball 416, cam, or other member of the connector 408 into engagement with the grooves 238, 240, thus helping to longitudinally align the attachment post 230 within the port 412.

As shown in FIG. 2A, the lower groove 240 and central groove 238 can be longitudinally displaced along the side surface 234 such that the lower groove 240 is closer to the retractor body 210 than the central groove 238 is to the retractor body 210. Moreover, the upper surface 212 of the retractor body 210 can include a serrated surface or teeth 213. Similarly, the lower surface 466 of the connector 408 can include a serrated surface or teeth 469. In one embodiment, the lower groove 240 can be positioned along the side surface 234 such that the teeth 469 engage the teeth 213 and restrict rotation of the attachment post 230 when the lower groove 240 is engaged by the connector 408.

The central groove 238 provides an attachment location that results in the upper surface 212 of the retractor body 210 being offset from a lower surface 466 of the connector 408. In particular, the central groove 238 can be longitudinally displaced along the side surface 234 such that, when engaged by the connector 408, the teeth 469 of the connector 408 are positioned away from and not engaged with the teeth 213 of the retractor body 210. By engaging the grooves 238, 240, the connector 408 can prevent the attachment post 230 from longitudinally traversing the port 412. However, with the teeth 213, 469 disengaged and the central groove 238 running circumferential around the side surface 234 of the attachment post 230, the attachment post 230 can freely rotate about the longitudinal axis $A_A$. Thus, by aligning the attachment post 230 per the central groove 238 or the lower groove 240, a practitioner can selectively choose between (i) allowing the retractor 20 to freely rotate or swivel about the axis $A_A$, or (ii) locking the retractor 20 to the connector 408 and thereby preventing the retractor 20 from freely rotating or swiveling about the axis $A_A$.

Finally, the upper groove 236 can define a flange 242 to which a manipulator or handle can be attached. In one embodiment, the upper groove 236 is too small to receive the locking ball 416, cam, or other member of the connector 408, thus reducing the chance of accidental, vertical misalignment of the attachment post 230 within the port 412.

FIG. 2A depicts the attachment post 230 with three grooves 236, 238, 240. However, the attachment post 230' of FIG. 2B includes only grooves 236, 238. The attachment post 230' is suitable for embodiments that are not concerned with providing a selective swivel lock feature. For example, as shown in FIG. 2B, the retractor 20' can lack the serrated surface 213 of FIG. 2A. Thus, the retractor 20' can be used in procedures where locking or preventing swiveling of the retractor 20' is not warranted or is undesirable. It should be appreciated, that the post 230' can also be used with retractor blades having the serrated surface 213 of FIG. 2A. Such a retractor blade can lock or prevent swiveling of the retractor 20' when used with a connector 408 having teeth 469.

Figure 3:
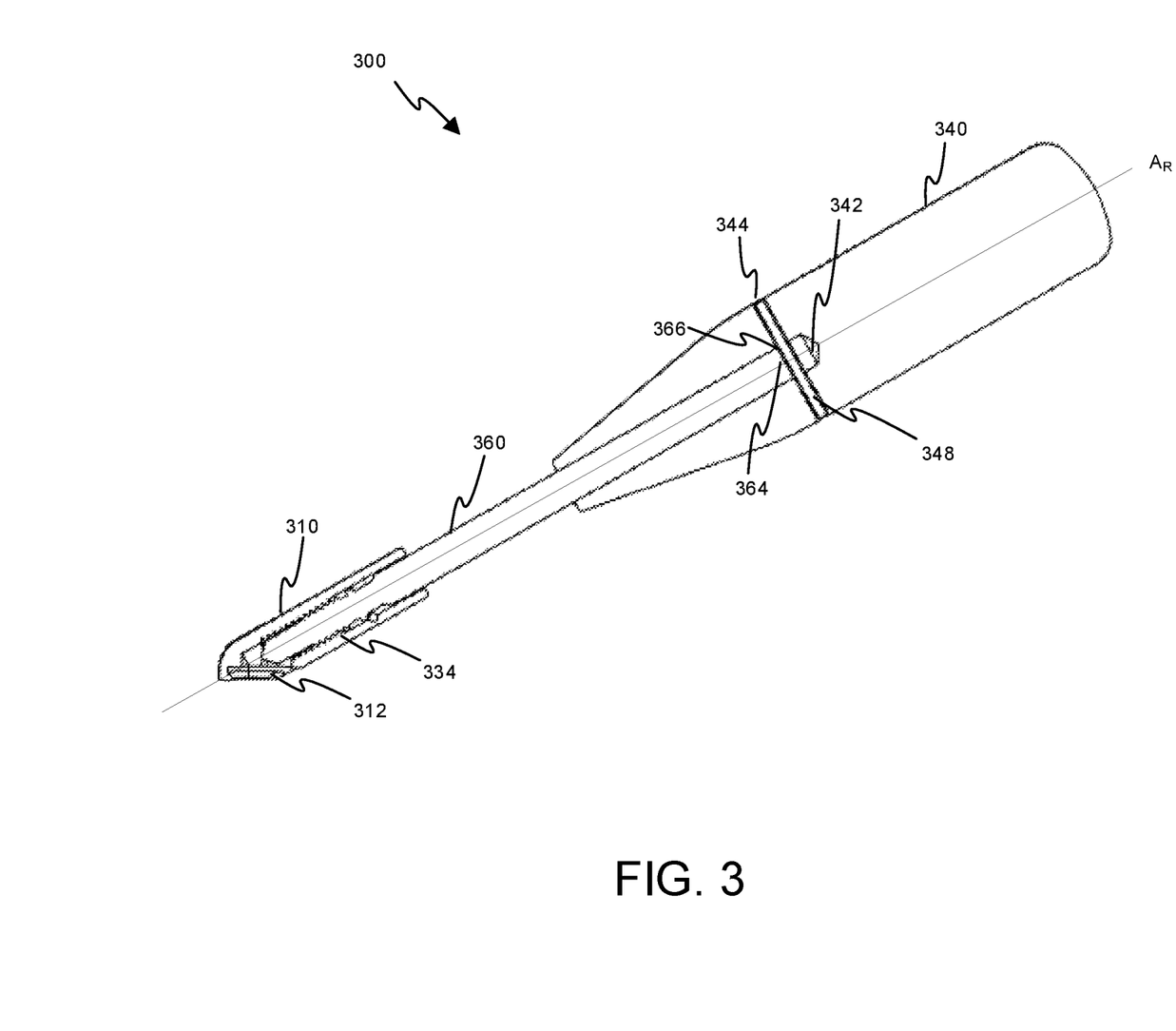
FIG. 3 depicts an example handle that can be coupled to retractors of the retractor system shown in FIG. 1.

FIG. 3 depicts a handle 300 suitable for attaching to retractors 20, 20' of FIGS. 2A and 2B. For example, the handle 300 can be attached to the retractor 20 via a slidable engagement with the flange 242. To this end, the handle 300 can include an attachment portion 310, a grip 340, and a retaining rod 360. The retaining rod 360 can secure the grip 340 to the retractor 20 via the attachment portion 310. Moreover, the retaining rod 360 can be manipulated to selectably engage the top surface 232 of the attachment post 230 to secure the handle 300 to the retractor 20.

The attachment portion 310 can be sized and adapted to cooperate with the attachment post 230. In particular, the attachment portion 310 can include a slot 312 that is sized and adapted to accept and mate with flange 242 of the attachment post 230.

The grip 340 can be sized and adapted to be grasped by a practitioner's hand. The grip 340 can include an aperture 342 sized to receive a proximal end 364 of the retaining rod 360. The grip 340 can further include an aperture 344 which can be aligned with a corresponding aperture 366 of the retaining rod 360 that is positioned toward the proximal end 364 of the retaining rod 360. A pin 348 can pass through the apertures 342, 366 thereby securing the grip 340 to the retaining rod 360. A practitioner can rotate the grip 340 about the longitudinal axis $A_R$ of the rod 360 in order to rotate and advance the retaining rod 360. In particular, threads 334 of retaining rod 360 can engage threads of the attachment portion 310 and advance the retaining rod 360 such that it engages the attachment post 230 and secures the handle 300 to the retractor 20.

After securing the handle 300 to the retractor 20, the grip 340 can permit convenient manipulation and placement of the blade 220. After positioning the blade 220, the practitioner can rotate the grip 340 about longitudinal axis $A_R$ to withdrawal the retaining rod 360 from the attachment portion 310 and disengage the retaining rod 360 from the attachment post 230. After such disengagement, the handle 300 can be detached from the retractor 20. The practitioner can then attach the retractor 20 to the connector 408 of a retractor arm 40 via the port 412.

Figure 4:
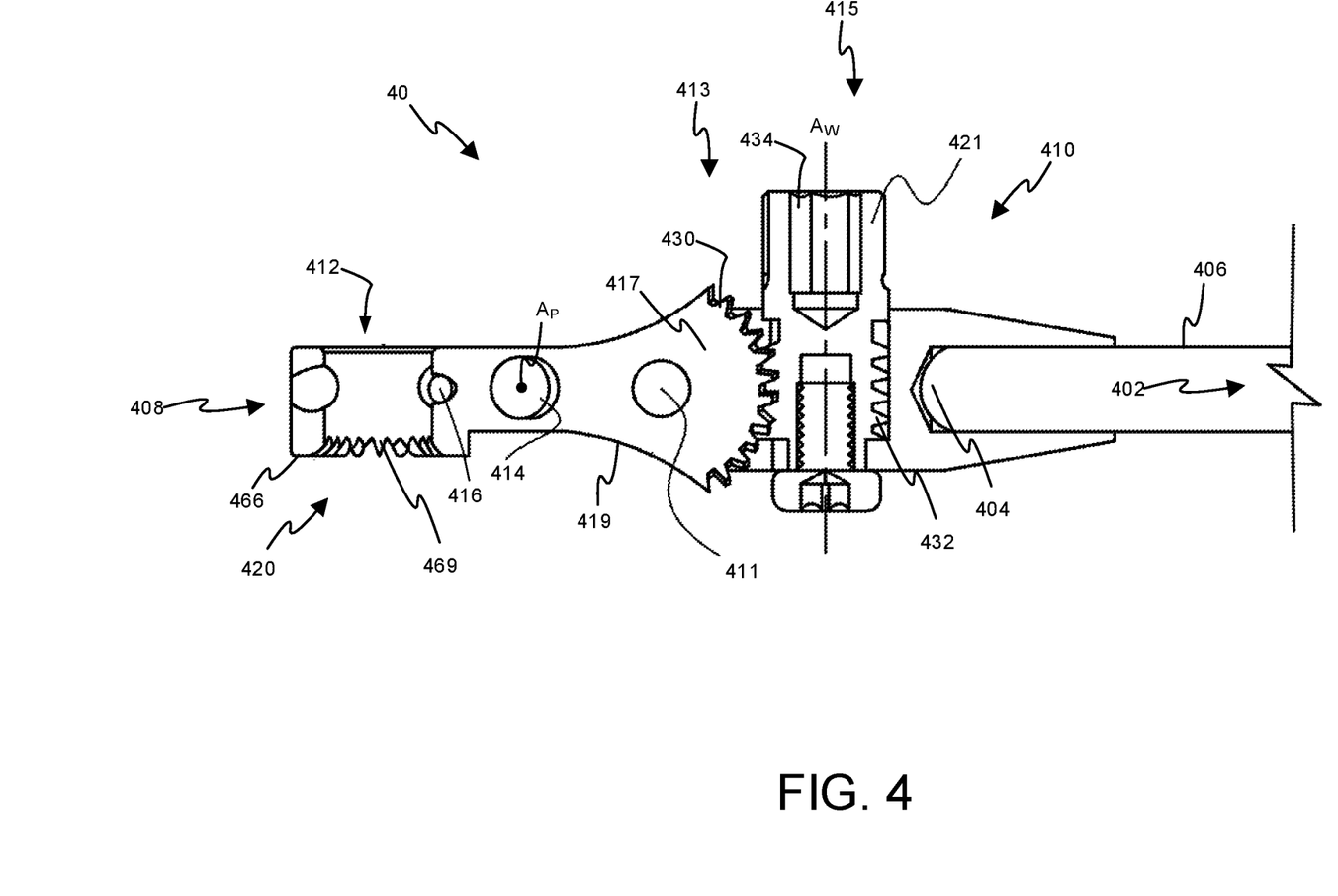
FIG. 4 depicts an example retractor arm of the retractor system shown in FIG. 1.

Referring now to FIG. 4, details regarding retractor arms 40 of FIG. 1 are presented. In general, each retractor arm 40 can adjustably constrain a proximal end of a retractor 20 that is secured to the retractor arm 40. In some embodiments, the retractor arm 40 can provide the retractor 20 at least some appreciable freedom of motion relative to the frame assembly 2 in at least one direction. While preventing at least some motion of the retractor 20, the retractor arm 40 can permit the retractor 20 some freedom of motion but maintain the retractor 20 at or near a selected position. In other embodiments, the retractor arm 40 can be adapted to maintain the retractor 20 in a fixed or stationary position once various joints are arranged in a desired position.

The retractor arm 40 can include one or more adjustable joints 410, which can be adjusted to a desired position. In some embodiments, the retractor arm 40 can include other types of adjustable joints. For example, the retractor arm 40 can include one or more a universal joints, ball joints, prismatic joints, etc. located along the length of the retractor arm 40.

As shown, the retractor arm 40 can include an elongated shaft 406 that extends from a proximal end 402 toward a distal end 404. A connector 408 can be adjoined to the distal end 404 of the shaft 406 via the adjustable joint 410. The connector 408 can be adapted to receive and secure the retractor 20 to the shaft 406.

The shaft 406 can include a generally straight, generally cylindrical member. In some embodiments, the shaft 406 can be bent in one or more locations, or curved to accommodate different procedures or access sites.

The adjustable joint 410 can generally join the connector 408 to the shaft 406, allowing the shaft 406 and the connector 408 to be adjusted relative to one another in one plane, but restricting their freedom of motion in other directions. For example, the adjustable joint 410 can include a pin 411 and a worm drive 413. The worm drive 413 can control and adjust the amount of pivot or angle between the shaft 406 and connector 408. In particular, a worm 415 of the worm drive 413 can pass through the adjustable joint 410 such that a longitudinal axis $A_W$ of the worm 415 can be perpendicular to the longitudinal axis $A_P$ of the pin 411. Furthermore, a worm gear 417 of the worm drive 413 can be positioned along the proximal end 419 of the connector 408 such that teeth 430 of the worm gear 417 mesh with threads 42 of the worm 415. Rotation of the worm 415 via the head 421 in a first direction can adjust or force the connector 408 in a downward direction with respect to the shaft 406. Conversely, rotation of the worm 415 in a second direction opposite the first direction can adjust or force the connector 408 in an upward direction with respect to the shaft 406.

The head 421 of the worm 415 can include a cavity 434 to receive the tool 790 (FIG. 4). The tool 790 can be inserted into the cavity 434 and rotated about axis $A_W$ to impart torque upon the worm 415 and rotate the worm 415 about the axis $A_W$.

The connector 408 can include an attachment hole or port 412, a button 414, and a locking ball 416. In the illustrated embodiment, the port 412, button 414, and locking ball 416 cooperate to form a clamp 420 that can selectively receive and retain an attachment post 230 of a retractor 20. Through the use of an internal mechanism (not shown), depressing the button 414 can allow increased freedom of movement of the locking ball 416, which can permit an attachment post 230 to be inserted into or removed from the port 412. Releasing the button 414 can constrain movement of the locking ball 416 and urge the locking ball 416 into the port 412. Protrusion of the locking ball 416 into the port 412 can cause the locking ball 416 to engage a groove 238, 240 of the attachment post 230 of retractor 20 and secure the attachment post 230 in the port 412.

Figure 5:
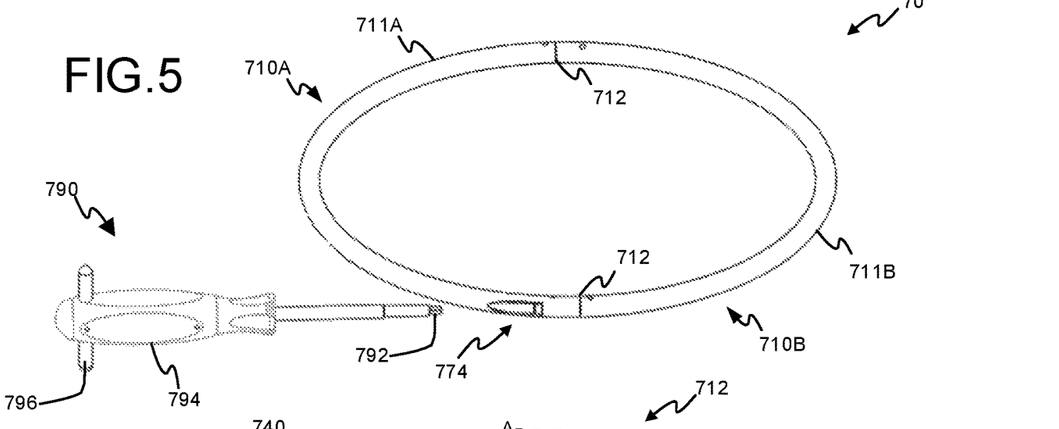
FIGS. 5-7 depict example ring segments of the retractor system shown in FIG. 1.

Turning now to FIG. 5, an assembled ring frame 70 of the retractor system 1 is shown. The ring frame 70 can include multiple ring segments 710A, 710B and joints 712. In one embodiment, the ring frame 70 can include two ring segments 710. Each ring segment 710A, 710B can be semi-circular, thus resulting in a circular ring frame 70 when the two ring segments 710A, 710B are joined to one another at joints 712. However, in some embodiments the shape of the ring frame 70 can be non-circular and thus the shape of the ring segments 710A, 710B can differ accordingly. For example, the ring frame 70 can have an elliptical shape, a rectangular-shape, a square shape, etc. Moreover, instead of rectangular, square, etc. ring frames 70 having sharp (e.g. 90°) corners, such ring frames 70 can include rounded corners that permit sliding attached clamps 80 along such corners.

FIG. 5 depicts the ring frame 70 with two ring segments 710A, 710B; however, the ring frame 70 in some embodiments can be formed from three, four, five, etc. ring segments. The ring segments can be of identical lengths or varying lengths. In some embodiments, each ring segment can have a same construction. In particular, the ring segments can be essentially identical, but can have slight variances due to manufacturing tolerances. Such a construction can ease assembly of the ring frame 70 from the ring segments since the order in which the ring segments are joined via tool 790 can be immaterial.

The joined ring segments 710A, 710B can provide outer surfaces 711A, 711B of the ring frame 70 with a generally uniform radial cross section. In one embodiment, the ring segments 710A, 710B have circular, radial cross sections and provide a radial cross sections having a uniform diameter along the length of the segments 710A, 710B. However, ring segments 710A, 710B having other cross sections such as square, retangular, ellipitical, etc. are contemplated. The uniform radial cross section of the ring segments 710A, 710B can permit clamps 80, 82 to be slid along the ring segments 710A, 710B and secured anywhere along the length of each segment 710A, 710B. The ring segments 710A, 710B can further provide joints 712 that are contained within the generally uniform radial cross section of the ring segments 710A, 710B and in particular lack protrusions that would prevent clamps 80, 82 from sliding along the segments 710A, 710B and across the joints 712. In some embodiments, the joints 712 have radial cross section with the same uniform diameter as the ring segments 710A, 710B. Such a radial cross section of a joint 712 not only permits clamps 80, 82 to slide across the joint 712 but also permits clamps 80, 82 to be secured at the joint 712.

Figure 6:
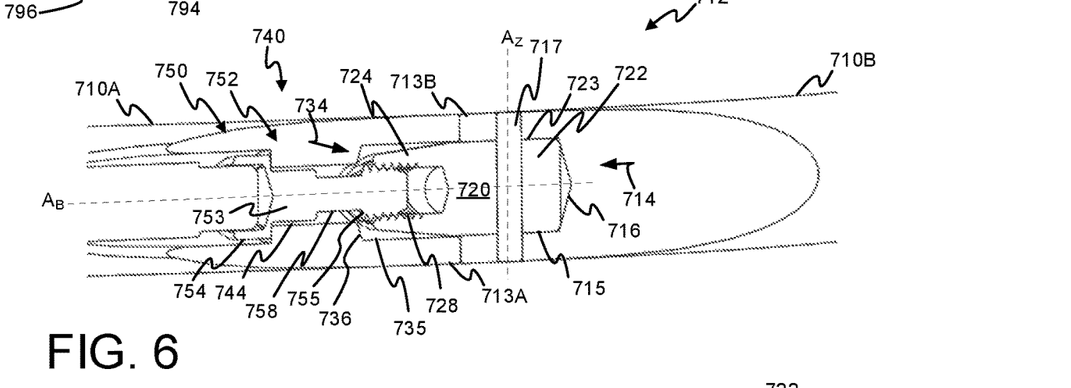
Figure 7:
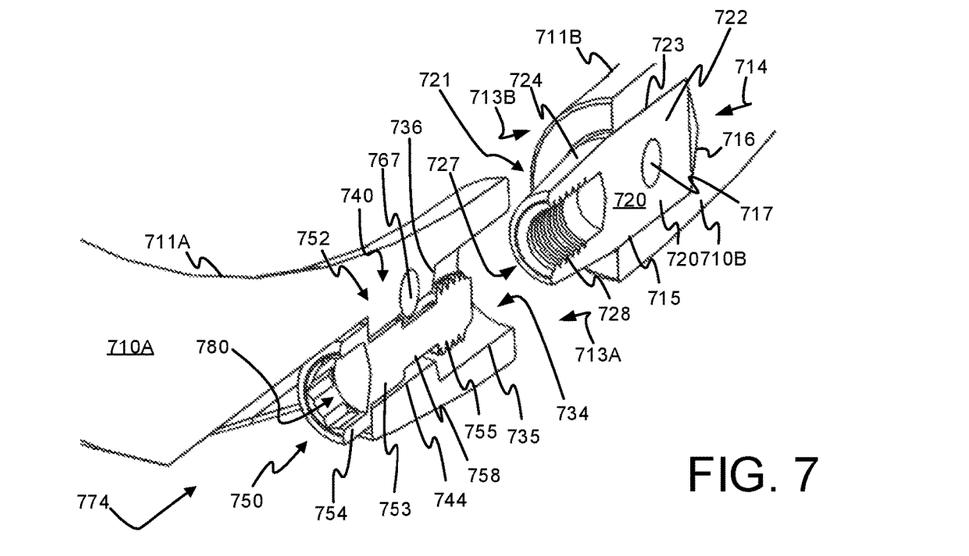

Referring now to FIGS. 6 and 7 further details regarding joints 712 are shown. The joint 712 can include an alignment bushing 720 and a joining screw 750. In generally, the joining screw 750 engages the alignment bushing 720 and joins two ring segments 710A, 710B together when rotated in a tightening direction via tool 790.

A bore 714 can be drilled or otherwise formed into one end 713B of the ring segment 710B. As shown, the bore 714 can include a cylindrical, inner surface 715 and tapered, end surface 716. The alignment bushing 720 can be partially inserted into the bore 714 and affixed to the ring segment 710B. In particular, the alignment bushing 720 can have a generally cylindrical shape with a cylindrical portion 722 and a tapered portion 724. The cylindrical portion 722 can have a diameter slightly less than the diameter of the inner surface 715 of the bore 714 such that an outer surface 723 of the cylindrical portion 722 closely mates with the inner surface 715 of the bore 714. Moreover, the cylindrical portion 722 of the bushing 720 can have a length that is slightly longer than the length of the inner surfaces 715 of the bore 714. Thus, the cylindrical portion 722 can extend beyond the end 713B of the ring segment 710B and engage the ring segment 710A.

As further shown in FIGS. 6 and 7, the joint 712 can further include a retaining pin 717 that passes through the alignment bushing 720 and longitudinal surfaces 711B of the ring segment 710B. In particular, a longitudinal axis Az of the pin 717 can be perpendicular to the longitudinal axis $A_B$ of the alignment bushing 720. The pin 717 can help hold the bushing 720 in place. In particular, the pin 717 can prevent the bushing 720 from being pulled from the bore 714. Moreover, the pin 717 can prevent the bushing 720 from rotating about its longitudinal axis $A_B$ with respect the inner surfaces 715 of the bore 714.

The alignment bushing 720 further includes a bore 727 drilled or otherwise formed in a distal end of its tapered portion 724. The bore 727 can include threads 728 along its internal surface. Moreover, a diameter of the bore 727 can be sized such that threads 728 of the bore 727 engage with threads 755 of the joining screw 750 during assembly. Moreover, a depth or length of the bore 727 can be great enough to permit receiving the joining screw 750 to a depth that results in the end 713A of ring segment 710A closely mating with end 713B of ring segment 710B.

Turning now to ring segment 710A, a bore 734 can be drilled or otherwise formed into the end 713A of the ring segment 710A. As shown, the bore 734 can include a cylindrical, inner surface 735 and tapered, end surface 736. During assembly of the ring frame 70, the tapered portion 722 as well as part of the cylindrical portion 722 of the alignment bushing 720 can be inserted into the bore 734. To permit such insertion, the bore 734 can have a diameter equal to the bore 714. As a result, the outer surface 723 of the cylindrical portion 722 can closely mate with the inner surface 735 of the bore 734. Moreover, the bore 734 can have a depth or length that is longer than a portion 721 of the alignment bushing 720 that extends from the end 713B of the ring segment 710B. Such a depth can permit full insertion of the extended portion 721 into the bore 734.

As further shown in FIGS. 6 and 7, a second bore 744 can be drilled or otherwise formed into the tapered surface 735 of the bore 734 to provide a bushing 740 for joining screw 750. As shown, the joining screw 750 can include a shaft 752 and a head 754 coupled to a proximal end of the shaft 752. The shaft 752 can further include a collar 753 proximate the head 754, threads 755 proximate a distal end of the shaft 752, and a retaining groove 758 between the collar 753 and the threads 755. Both the collar 753 and the threads 755 can have a greater diameter than the retaining groove 758. Moreover, the collar 753 and threads 755 can each have a diameter that is slightly smaller than a diameter of the second bore 744. As such, an outer surface of the collar 753 can closely mate with an inner surface of the bore 744 and thus limit radial movement of the joining screw 750 with respect to axis $A_B$.

The joint 712 can further include a retaining pin 767 that passes through longitudinal surfaces 711A of the ring segment 710A. In particular, a longitudinal axis of the pin 767 can be perpendicular to the longitudinal axis $A_B$ of the joining screw 750. Moreover, an outer surface of the retaining pin 767 can engage the retaining groove 758 of the joining screw 750 to help prevent the joining screw 750 from being withdrawn from the second bore 455. With the collar 753 and threads 755 having a diameter less than the diameter of the second bore 455, the joining screw 750 could be withdrawn from the second bore 455. However, with the collar 753 and threads 755 having a diameter greater than the diameter of the retaining groove 758, the retaining pin 767 can prevent the joining screw 750 from being withdrawn from the second bore 744 as there is insufficient room for the threads 755 to slide past the pin 767.

A recess 774 in a longitudinal surface 711A of the ring segment 710A can provide tool 790 access to the head 754 of the joining screw 750. The recess 774 can be drilled or otherwise formed into the longitudinal surface 711A of the ring segment 710A. As shown by line $A_B$, the ring segments 710A, 710B, the bores 714, 734, 744, the recess 774, the alignment bushing 720, the busing 740, and joining screw 750 can have a common longitudinal axis. However, in some embodiments, such components can be aligned such that not all of the components share a common longitudinal axis.

The head 754 and the tool 790 can be implemented to include one of a number of different screw drives. For example, the head 754 can include a cavity 780 via which the tool 790 can apply torque to the head 754. In particular, the tool 790 can include a tip 792 sized to engage and closely mate with the cavity 780 of the head 754. Some example screw drives for the head 754 and tool 790 include drives based on a slotted shape, a cross-slotted shape, a square shape, multiple-square shape, a hex shape, a double hex socket shape, etc. In the depicted embodiment, the cavity 780 can be hex shaped and the tool tip 792 can provide a hex shaped driver to engage the hex shaped cavity 780. Moreover, the cavity 434 of the worm 415 (FIG. 4) can conform to the same screw drive configuration as the tool tip 792 and the head 754. As such, the tool 790 used to assemble the ring frame 70 can also be used to adjust the retractor arms 40.

As further shown, the tool 790 can include a handle 794 which can be grasped and turned by hand in order to impart torque to the tool tip 792 and the head 754 to which its engaged. The tool 790 can further include a cross-bar 796 that passes through the handle 794 toward a proximal end of the handle 794. The cross-bar 796 can aid a practitioner in gripping the tool 790 and imparting torque to the tool tip 792 and head 754. By applying torque to the head 754, the joining screw 750 can be rotated in a tightening direction which causes the threads 755 to mesh with threads 728 of the alignment bushing 720 and draw the head 754 toward the alignment bushing 720. Such drawing of the joining screw 750 can force a lower surface of the head 754 against a seating surface of the bushing 740, thus drawing the ring segment 710A toward the ring segment 710B and the extended portion 721 of the alignment bushing 720 into the bore 734. Continued rotation in the tightening direction eventually closely mates the end 713A of ring segment 710A with the end 713B of ring segment 710B and completes the joining of the end 713A to the end 713B.

Conversely, by applying torque to the head 754 via tool 790, the joining screw 750 can be rotated in the loosening direction which causes the threads 755 to mesh with threads 728 of the alignment bushing 720 and push the joining screw 750 and the ring segment 710A away from the alignment bushing 720. Continued application of torque in the loosening direction eventually disengages threads 728 from threads 755. After disengaging threads 728, 755, the ring segments 710A, 710B can be pulled apart by hand, thus removing the extended portion 721 of the alignment bushing 720 from the bore 734 and completing the decoupling of the end 713A from the end 713B.

Figure 8:
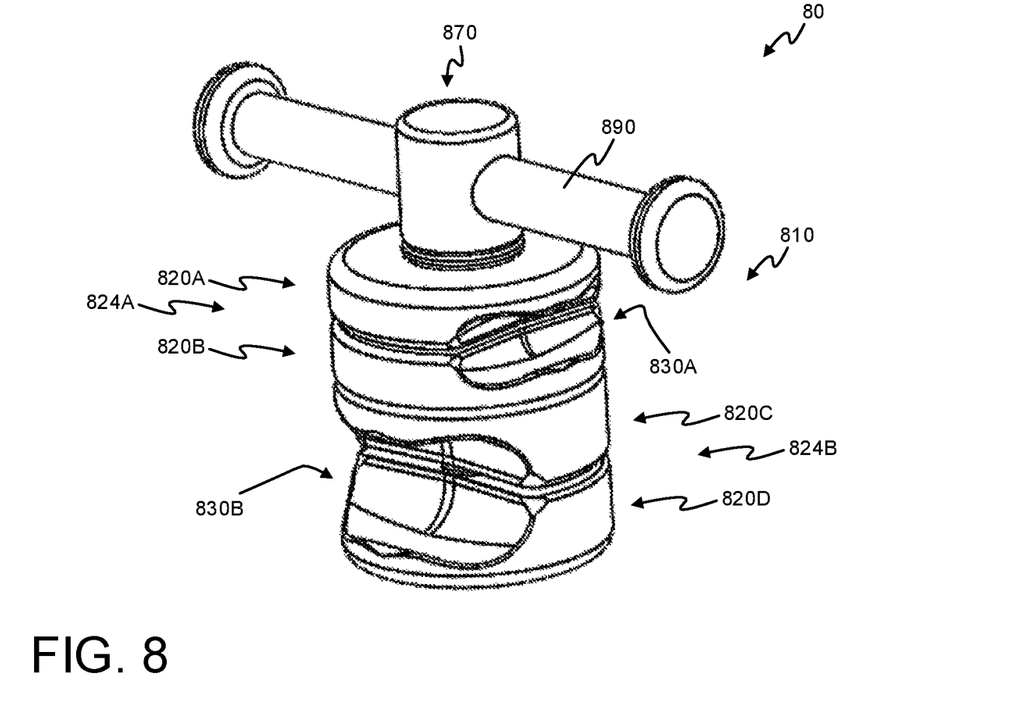
FIGS. 8-17 depict an example clamp of the retractor system shown in FIG. 1.
Figure 9:
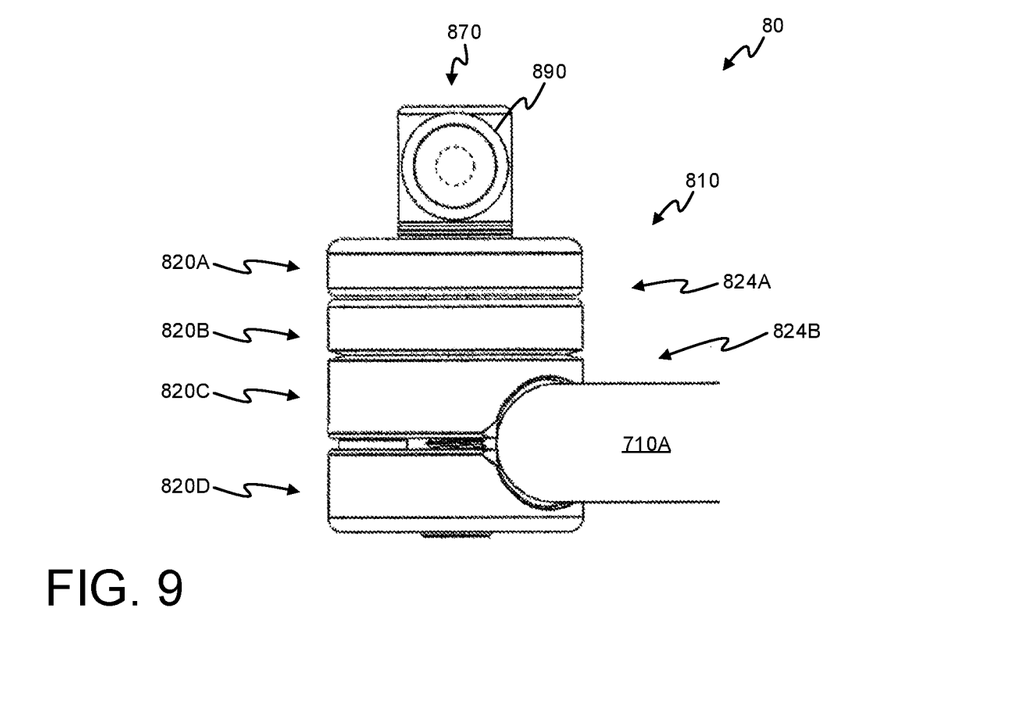

Referring now to FIGS. 8-17, details of the clamp 80 of the retractor system 1 are presented. As shown in FIGS. 8 and 9, the clamp 80 can include a segmented body 810, an adjustment screw 870, and a cross-bar 890 used to impart torque to the adjustment screw 870. The segmented body 810 can include four segments 820A-820D. The upper two body segments 820A, 820B can form first segment pair 822A and the lower two body segments 820C, 820D can form a second segment pair 822B. However, other embodiments can include a different number of segments and thus a different number of segment pairs.

Figure 11:
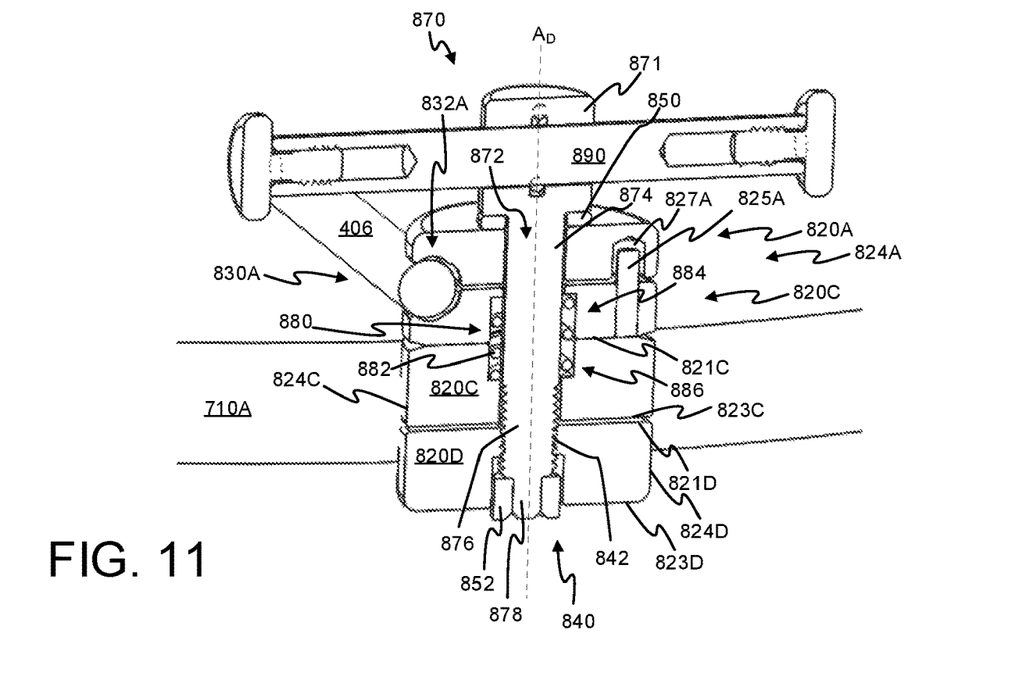

Referring now to FIG. 11, the first segment pair 822A can provide a first aperture 830A to receive an elongated member of the retractor system 1 such as, for example, the shaft 406 of the retractor arm 40. Moreover, the first segment pair 822A can include a first set of jaws 832A about the first aperture 830A, which are configured to receive and retain an elongated member in the first aperture 830A.

Figure 10:
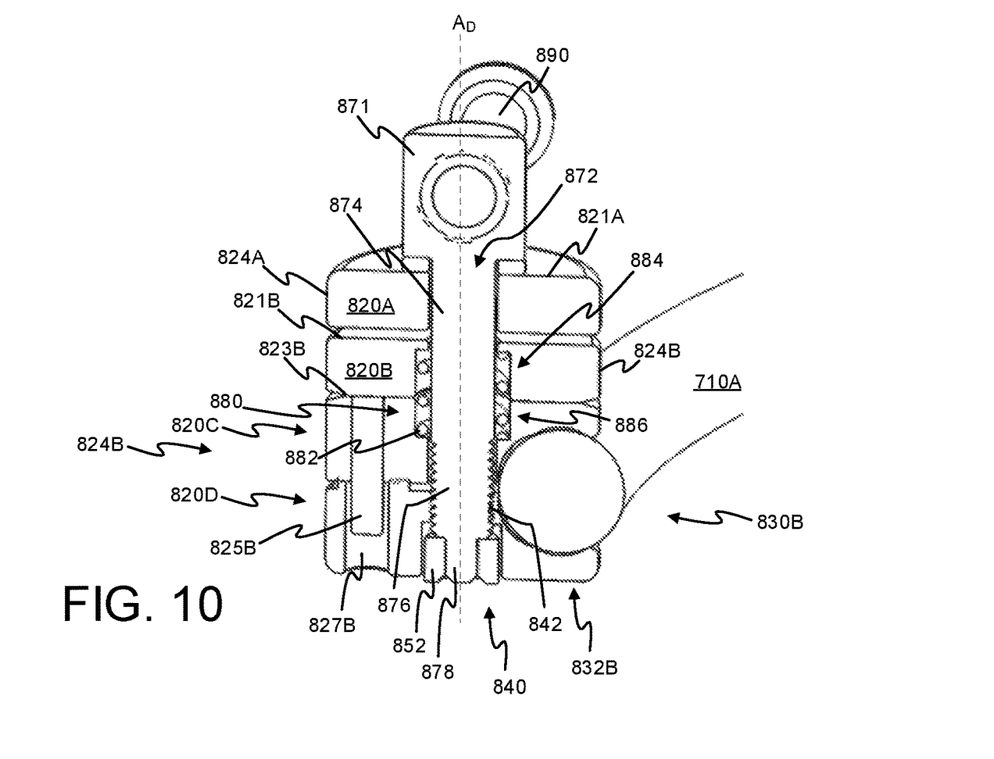

As shown in FIG. 10, the second segment pair 822B can provide a second aperture 830B to receive an elongated member of the retractor system 1 such as, for example, a ring segment 710A, 710B of the ring frame 70. Moreover, the second segment pair 822B can include a second set of jaws 832B about the second aperture 830B, which are configured to receive and retain an elongated member in the second aperture 830B.

Referring now to FIGS. 10 and 11, each of the segments 820A-820D can include an upper surface 821A-821D, a lower surface 823A-823D opposite the upper surface 821A-821D, and a side surface 824A-824D the joins the upper surface 821A-821D to the lower surface 823A-823D. As depicted, each of the segments 820A-820D can have cylindrical shape with a circular base, thus resulting in circular upper surfaces 821A-821D and circular lower surfaces 823A-832D. However, the body segments 820A-820D in other embodiments can have a different shaped bases (e.g., elliptical, square, rectangular, hexagonal, polygonal, etc.). The upper surfaces 821A-821D and lower surfaces 823A-823D each have the same shape and size thus resulting in the segmented body 810 having a right, cylindrical shape when the segments are stacked. In some embodiments, the shape or size of the upper surfaces 821A-821D and the lower surfaces 823A-823D can vary. For example, the radius of the upper surfaces 821A-821D and the lower surfaces 823A-823D can be decrease from bottom to top, thus resulting in the body 810 having a frustum shape. Other variances in shape and/or size are possible and contemplated.

A bore 840 can pass through each of the segments 820A-82D. In particular, the bore 840 can pass through upper surfaces 821A-821D and lower surfaces 823A-832D of the segments 820A-820D. Moreover, a longitudinal axis of the bore 840 can be aligned with a central axis of each of the surfaces 821A-821D, 823A-823D as shown by line $A_D$. The bore 840 can receive a shaft 872 of the adjustment screw 870 such that the shaft 827 passes through a central portion of each of the segments 820A-820D. More specifically, the shaft 872 can include an upper portion 874, a threaded portion 876, and a distal end 878. The upper portion 874 of the shaft 872 can mate with inner surfaces of the bore 840 associated with the segments 820A-820B. The threaded portion 876 of the shaft 872 can mate with an inner surface of the bore 840 associated with body segment 820C. Moreover, threads of the threaded portion 876 can mesh with threads 842 of the body segment 820D.

A washer 850 can be placed between the upper surface 821A of the upper body segment 820A and a lower surface of head 871 of the adjustment screw 870. The cross-bar 890 can pass through the head 871 such that the longitudinal axis $A_D$ of the cross-bar 890 is perpendicular with the longitudinal axis $A_D$ of the adjustment screw 870. The washer 850 can distribute a clamping force applied by the head 871 to the upper surface 821A. More specifically, a practitioner can grasp the cross-bar 890 and rotate the adjustment screw 870 in a tightening direction. Such rotation can cause the thread of threaded portion 876 to mesh with threads 842 of the body segment 820D and draw the body segment 820D toward head 871 and washer 850. Such drawing can reduce the distance between upper body segment 820A and lower body segment 820B, thus reducing the distance between jaws of the first set of jaws 832A and jaws of the second set of jaws 832B. The first set of jaws 832A and second set of jaws 832B can thereby engage or increase a clamping force applied to elongated members received in respective apertures 830A, 830B.

Conversely, a practitioner can grasp the cross-bar 890 and rotate the adjustment screw 870 in a loosening direction. Such rotation can cause the threads of threaded portion 876 to mesh with threads 842 of the body segment 820D and push the body segment 820D away from head 871 and washer 850. Such pushing can increase the distance between upper body segment 820A and lower body segment 820D, thus increasing the distance between jaws of the first set of jaws 832A and jaws of the second set of jaws 832B. The first set of jaws 832A and second set of jaws 832B can thereby decrease a clamping force applied to or disengage from elongated members received in respective apertures 830A, 830B. A stop 852 affixed to the distal end 878 of the shaft 872 can prevent the practitioner from inadvertently disassembling the clamp 80 by over-extracting the adjustment screw 870 and disengaging the threads of the threaded portion 876 from the threads 842 of the body segment 820D.

As further shown in FIGS. 10 and 11, a cavity 880 can be formed along the bore 840 between the upper segment pair 822A and the lower segment pair 822B. In particular, the cavity 880 can include an upper portion 884 that extends through the lower surface 823B of the body segment 820B and a lower portion 886 that extends through the upper surface 821C of the body segment 820C. The cavity 880 can house a biasing spring 882 that provide a biasing force to upper seat surface 885 and a lower seat surface 887 of the cavity 880. The biasing force can bias the first segment pair 822A away from the second segment pair 822B. Moreover, the biasing force can maintain the first set of jaws 832A and the second set of jaws 832B in a closed position to prevent the elongated members in the apertures 830A, 830B from being removed without overcoming the biasing force. As such, the biasing spring 882 can help prevent inadvertent removal of elongated members from the apertures 830A, 830B.

Each segment pair 822A, 822B can include a pin 825A, 825B. As shown in FIG. 11, a pin 825A can be affixed to the lower body segment 820B of the upper segment pair 822A such that the pin 825A extends upwardly from the upper surface 821B of the lower body segment 820B. The upper body segment 820A of the segment pair 822A can include a bore 827A in the lower surface 823A. The bore 827A can receive the portion of the pin 825A protruding beyond the upper surface 821B of the lower body segment 820B. The bore 827A and pin 825A can cooperate to prevent the upper body segment 820A from rotating about the axis $A_D$ with respect to the lower body segment 820B, while permitting vertical movement (i.e., movement along the axis $A_D$) between the upper body segment 820A and the lower body segment 820B. In other embodiments, the pin 825A can be affixed to the upper body segment 820A and the bore 827A can be in the lower body segment 820B in a manner similar to pin 825B of FIG. 10.

Similarly, as shown in FIG. 10, a pin 825B can be affixed to the upper body segment 820C of the segment pair 822B such that the pin 825A extends downwardly from the lower surface 823C of the upper body segment 820C. The lower body segment 820D of the segment pair 822A can include a bore 827B through the upper surface 821D. The bore 827B can receive the portion of the pin 825B protruding beyond the lower surface 823C of the upper body segment 820C. The bore 827B and pin 825B can cooperate to prevent the upper body segment 820C from rotating about the axis $A_D$ with respect to the lower body segment 820D, while permitting vertical movement (i.e., movement along the axis $A_D$) between the upper body segment 820C and the lower body segment 820D. In other embodiments, the pin 825B can be affixed to the lower body segment 820D and the bore 827B can be in the upper body segment 820C in a manner similar to pin 825A of FIG. 11.

Figure 12:
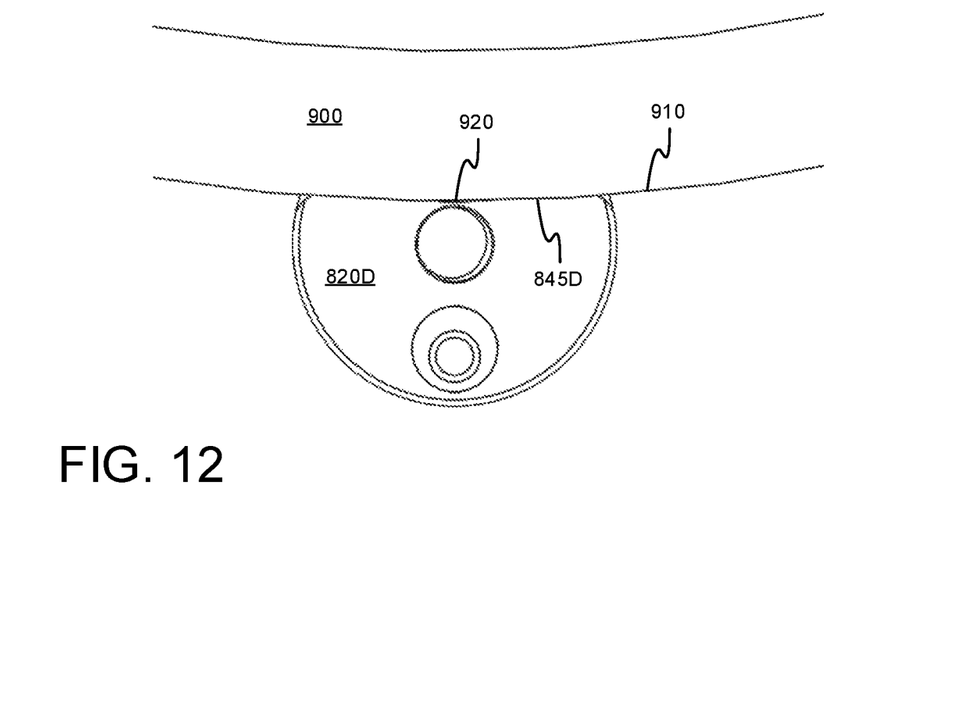
Figure 13:
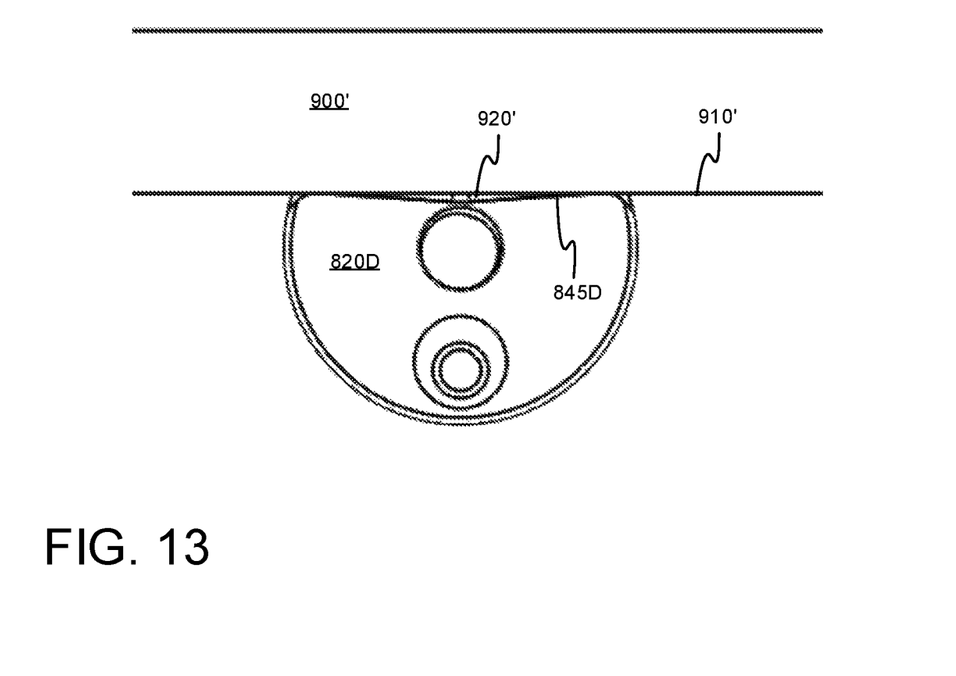
Figure 14:
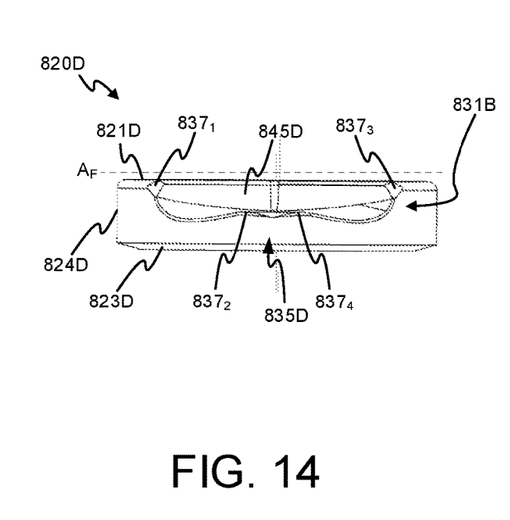

Referring now to FIGS. 12 and 13, a cross-sectional view the lower body segment 820D and its engagement of an elongated member is shown. In particular, FIG. 12 depicts the lower body segment 820D engaged with a curved, elongate member 900 such as a ring segment 710A, 710A. Conversely, FIG. 13 depicts the lower body segment 820D engaged with a straight, elongated member 900' such as a shaft 406 of a retractor arm 40 or a straight segment of a retractor frame. While FIGS. 12 and 13 depict lower body segment 820D, body segments 820A-820C can engage elongated members 900, 900' in a similar manner. Further details regarding such engagement are addressed via reference to various aspects of lower body segment 820D depicted in FIGS. 14-17. However, aspects of FIGS. 14-17 are also generally representative of body segments 820A-820C.

Figure 15:
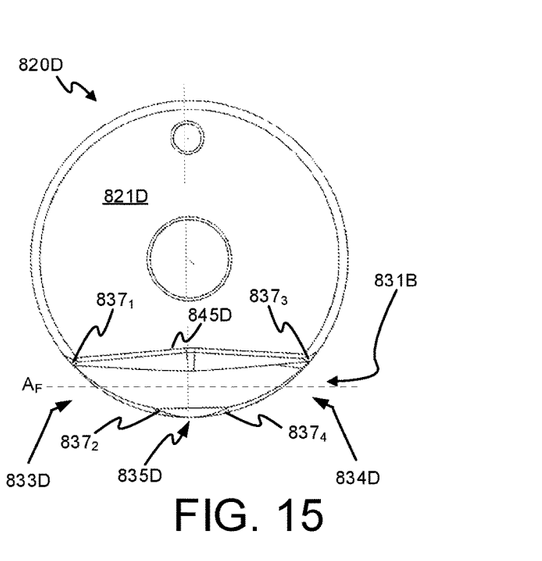
Figure 16:
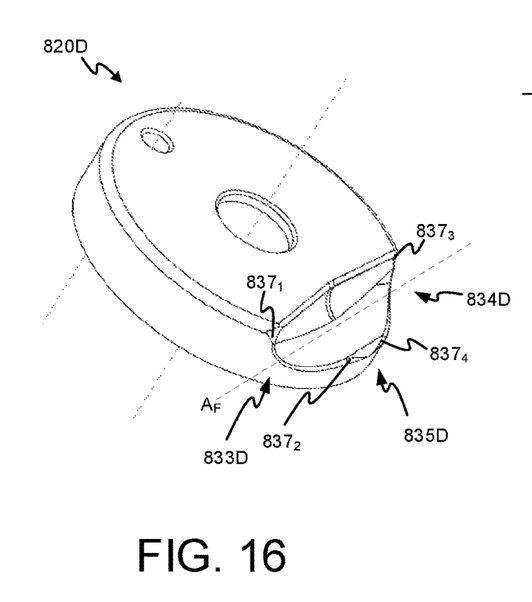

As shown in FIGS. 15 and 16, the aperture portion 831B can have a longitudinal axis $A_F$ along a chord of the circular, upper surface 821D that is perpendicular to the longitudinal axis $A_D$ of the segmented body 810. The aperture portion 831B corresponds to the lower portion of the second aperture 830B. In one embodiment, the aperture 830B through the segment pair 822B can have a generally cylindrical shape with elliptical ends that is defined by the aperture portion 831B in the lower body segment 820D and an aperture portion 831A in the upper body segment 820C. See, FIG. 17. The aperture portions 831A and 831B can be mirror images of one another. As such, aperture portions 831A and 831B can define roughly half of the aperture 830B.

The aperture portion 831A can traverse an upper surface 821D of the body segment 820D such that the aperture portion 831A does not extend through to the lower surface 823D of the body segment 820D. The aperture portion 831A can pass through the side surface 824D of the body segment 820D to form opposing entry port portions 833D and exit port portions 834D in the side surface 824D. Moreover, the aperture portion 831A can be positioned radially inward from the side surface 824D so as to leave at least a portion 835D of the side surface 824D radially outward or radially beyond the aperture portion 831A.

The lower body segment 820D can further include four teeth $837D_{1-4}$ positioned about the entry and exit port portions 833D, 834D. As shown, a first tooth $837D_1$ can be positioned along a radially-inner edge of the entry port portion 833D and a second tooth $837D_2$ can be positioned along a radially-outer edge of the entry port portion 833D along the radially-outer, portion 835D of the lower body segment 820D. Similarly, a third tooth $837D_3$ can be positioned along a radially-inner edge of the exit port portion 834D and a fourth tooth $837D_4$ can be positioned along a radially-outer edge of the export port portion 834D along the radially-outer, portion 835D of the lower body segment 820D.

Figure 17:
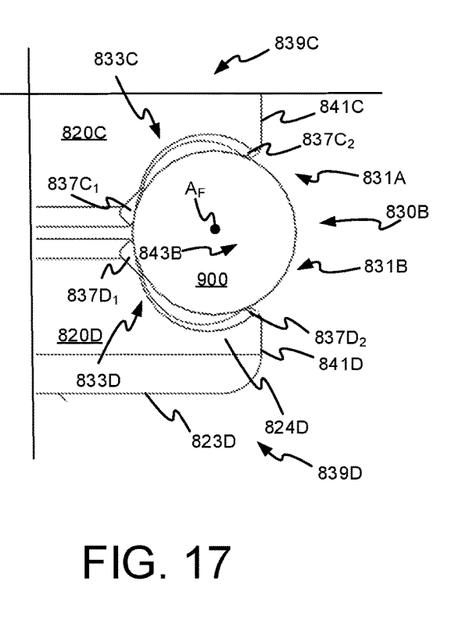

As noted above, the upper body segment 820C can be implemented in a similar manner. As such, the upper body segment 820C can include four teeth positioned in a similar manner. As shown in FIG. 17, the upper body segment 820C and lower body segment 820D can respectively provide an upper jaw 839C and a lower jaw 839C of the set of jaws 832B. The lower jaw 839D can include teeth $837D_1$, $837D_2$ about the entry port portion 833D that engage an elongated member 900 in aperture 830B. Similarly, the upper jaw 839C can include teeth $837C_1$, $837C_2$ about an entry port portion 833C that engage the elongated member 900 in aperture 830B. While not shown in FIG. 17, the elongated member 900 can be engaged by two teeth of the upper jaw 839C and two teeth $837D_{3-4}$ of the lower jaw 839D about exit port portions of the body segments 820C, 820D. As such, the clamp 80 can engage the elongated member 900 at multiple contact points (e.g., at two, three, four, etc. contact points) about the entry port portions and the exit port portions. The multiple contact points have proven to maintain the elongated members 900 in a stationary position better than embodiments that circumfertially engage the entire or most of the entire outer surface of the elongated member 900.

As shown in FIG. 17, the upper body segment 820C can provide an upper jaw 839C with a distal end 841C and the lower body segment 820D can provide a lower jaw 839D with a distal end 841D that spaced apart from the distal end 841C. As such, an opening 843B between the distal ends 841C, 841D can permit lateral insertion and removal of the elongated member 900 to and from the aperture 830B. In particular, the adjustment screw 870 can be loosened to a point where insertion or removal of the elongated member 900 merely requires overcoming the biasing force of the spring 882. In such a state, the biasing spring 883 can help retain clamp 80 about elongated member 900 while permitting the clamp 80 to be slid longitudinally along the elongated member 900. Conversely, the adjustment screw 870 can be tightened to a point where teeth of the jaws 839C, 839D engage the elongated member 900 with a clamping force sufficient to prevent removal of the elongated member 900 from the aperture 830B via opening 843B. Moreover, the clamping force can be sufficient to generally prevent sliding the clamp 80 longitudinally along the elongated member 900 or axially rotating the clamp 80 about the elongated member 900.

Finally, with reference back to FIGS. 12 and 13, an inner surface 845D of the aperture portion 831D can slant away from the radially-outer portion 835D to provide a concaved surface opposite the portion 835D. Such concaved inner surface 845D can receive a radially-outer surface 910 of a curved, elongated member 900 as shown in FIG. 12. When engaging a straight, elongated member 900', a gap 920' (FIG. 13) between an outer surface 910' of the member 900' and the inner surface 845D can be larger than a gap 920 (FIG. 12) between radially-outer surface 910 and the inner surface 845D.

To use the retractor system 1, the frame assembly 2 is first secured to the hospital bed. The ring frame 70 can then be assembled and attached to the frame assembly 2. In particular, the ring segment 710A can be secured to the ring segment 710B using the tool 790 to obtain an assembled ring frame 70. The assembled ring frame 70 can then be secured to a frame assembly 2 via one or more clamps 82 and their respective lower apertures 830B. With the patient in place, an incision can be made to provide access to the operative site of interest. Retractors 20 can be selected and secured to handles 300. The retractors 20 can be inserted, distal end 222 first, into the operative site of interest, and positioned as desired via handles 300 to retract tissue and provide access to the surgical site of interest. After positioned, a handle 300 can be detached from its retractor 20 and the retractor 20 can be secured to a connector 408 of a retractor arm 40. If needed, the practitioner can again use the tool 790 to adjust the angle of the connectors 408 with respect to shafts of the retractor arms 40. The practitioner can attach and position a clamp 80 along the ring frame 70 via the lower aperture 830B of the clamp 80. The shaft 406 of the retractor arm 40 can then be coupled to the ring frame 70 via an upper aperture 830A of the clamp 80. Alternatively, shafts 406 can be coupled to the ring frame 70 via clamps 80 before connecting the retractor arms 40 to retractors 20 via connectors 408.

While the present disclosure has been described with reference to certain embodiments, it will be understood by those skilled in the art that various changes can be made and equivalents can be substituted without departing from the scope of the present disclosure. In addition, many modifications can be made to adapt a particular situation or material to the teachings of the present disclosure without departing from its scope. Therefore, it is intended that the present disclosure not be limited to the particular embodiments disclosed, but that the present disclosure includes all embodiments falling within the scope of the appended claims.

What is claimed is:

1. A retractor system, comprising:
a ring frame comprising a first ring segment and a second ring segment detachably joined to the first ring segment at a joint contained within a cross section of the ring frame, wherein the ring frame provides a ring top surface and a ring bottom surface; and
a clamp comprising a first set of jaws defining a first aperture through which the ring frame passes when the first set of jaws are clamped to the ring frame,
wherein, when unclamped, the first set of jaws permit a radially-outer portion of the ring frame to pass therebetween and into the first aperture, and
wherein, wherein when clamped, the first set of jaws clamp against the ring top surface and the ring bottom surface with a first clamping force.

2. The retractor system of claim 1, wherein the joint of the ring frame comprises:
a joining screw in a recess toward an end of the first ring segment, the joining screw comprising a shaft, threads along at least a portion of the shaft, and a head that is accessible via the recess; and
a bushing toward an end of the second ring segment, the bushing comprising a bore and threads along at least a portion of the bore,
wherein rotation of the joining screw in a tightening direction causes the threads of the joining screw to engage the threads of the bushing and affix the first ring segment to the second ring segment.

3. The retractor system of claim 1, wherein the joint permits traversal of the first set of jaws across the joint with the ring frame received within the first aperture.

4. The retractor system of claim 1, wherein:
the first set of jaws comprise a first jaw having first teeth and a second jaw having second teeth; and
tips of the first and second teeth clamp against the ring top surface and the ring bottom surface and apply the first clamping force.

5. The retractor system of claim 1, wherein:
the clamp further comprises an adjustment screw;
the first set of jaws comprise a first jaw and a second jaw opposite the first jaw;
a distal end of the first jaw and a distal end of the second jaw are spaced apart to provide an opening to the first aperture;
rotation of the adjustment screw in a tightening direction reduces the opening between the first jaw and the second jaw to less than a vertical thickness of the ring frame to prevent passage of the ring frame through the opening, wherein the vertical thickness corresponds a distance between an uppermost portion of the ring top surface and an opposite lowermost portion of the ring bottom surface; and
rotation of the adjustment screw in a loosening direction increases the opening between the first jaw and the second jaw to greater than the vertical thickness of the ring frame to permit passage of the ring frame through the opening.

6. The retractor system of claim 1, wherein:
the first set of jaws comprise a first jaw and a second jaw opposite the first jaw;
a distal end of the first jaw and a distal end of the second jaw are spaced apart to provide an opening to the first aperture; and
the first set of jaws provide a concaved surface opposite the opening that permits the first aperture to receive a curved portion of the ring frame.

7. The retractor system of claim 6, wherein:
the first set of jaws comprise a first jaw having first teeth and a second jaw having second teeth; and
the first set of jaws engage a curved portion or a straight portion of the ring frame via tips of the first and second teeth.

8. The retractor system of claim 1, further comprising:
a retractor arm comprising a shaft and a connector that detachably couples a retractor to the shaft,
wherein the clamp further comprises a second set of jaws defining a second aperture configured to receive the shaft of the retractor arm, and
wherein the second set of jaws engage an outer surface of the shaft of the retractor arm and apply a second clamping force to the outer surface of the shaft of the retractor arm received by the second aperture.

9. The retractor system of claim 8, wherein:
the joint of the ring frame comprises a joining screw having a first head configured to be engaged and rotated by a tool;
rotation of the first head by the tool causes the joining screw to join the first ring segment to the second ring segment;
the retractor arm further comprises an adjustable joint and an adjustment screw having a second head configured to be engaged and rotated by the tool; and
rotation of the second head by the tool causes the adjustment screw of the retractor arm to adjust an angle of the connector with respect to the shaft of the retractor arm.

10. The retractor system of claim 2, wherein a longitudinal axis of the joining screw is perpendicular to the cross section.

11. A ring frame for a retractor system, the ring frame comprising:
ring segments detachably joined to one another at a plurality of joints;
wherein the ring segments provide the ring frame with a generally uniform outer surface having generally uniform circular cross sections;
wherein each joint of the plurality of joints is contained within the generally uniform circular cross sections of the generally uniform outer surface;
wherein a joint of the plurality of joints comprises:
a joining screw in a recess of a first ring segment, the joining screw comprising a shaft, threads along at least a portion of the shaft, and a head that is accessible via the recess; and
a bushing of a second ring segment, the bushing comprising a bore and threads along at least a portion of the bore; and
wherein rotation of the joining screw in a tightening direction causes the threads of the joining screw to engage the threads of the bushing and join the first ring segment to the second ring segment.

12. The ring frame of claim 11, wherein the ring segments form a circular ring when joined.

13. The ring frame of claim 12, wherein the ring segments each have a same construction.

14. The ring frame of claim 11, wherein the ring segments, when joined, provide the outer surface of the ring frame with a uniform diameter along each ring segment and at each of the plurality of joints.

15. The ring frame of claim 11, wherein:
a longitudinal axis of the joining screw and a longitudinal axis of the bore are coaxial; and the longitudinal axis of the joining screw and the longitudinal axis of the bore pass through a center of a circular cross section through the joint.

16. A retractor system, comprising a ring frame comprising a first ring segment and a second ring segment detachably joined to the first ring segment at a joint contained within a cross section of the ring frame, wherein the cross section corresponds to a cutting plane that is perpendicular to an outer surface of the ring frame; and a clamp comprising a segmented body and an adjustment screw;

wherein the segmented body comprises a first segment, a second segment, and a bore through the first segment and the second segment;

wherein the first segment comprises a first segment upper surface, a first segment lower surface, a first segment upper jaw, and a first segment side surface coupling the first segment upper surface to the first segment lower surface;

wherein the second segment comprises a second segment upper surface, a second segment lower surface, a second segment lower jaw, and a second segment side surface coupling the second segment upper surface to the second segment lower surface;

wherein the first segment upper jaw and the second segment lower jaw define a first aperture that passes through the first segment side surface and the second segment side surface;

wherein the first segment upper jaw includes first segment upper teeth;

wherein the second segment lower jaw includes second segment lower teeth;

wherein the adjustment screw passes through the first segment and the second segment via the bore; and wherein rotation of the adjustment screw in a tightening direction causes tips of the first segment upper teeth and tips of the second segment lower teeth to apply a first clamping force to the outer surface of the ring frame passing through the first aperture.

17. The retractor system to claim 16, wherein:

the first segment upper jaw comprises an upper jaw distal end;

the second segment lower jaw comprises a lower jaw distal end;

the upper jaw distal end and the lower jaw distal end are spaced apart to provide an opening to the first aperture;

rotation of the adjustment screw in the tightening direction prevents passage of the ring frame through the opening; and rotation of the adjustment screw in a loosening direction permits passage of the ring frame through the opening.

18. The retractor system of claim 17, wherein:

the first segment and the second segment each provide a concaved surface opposite the opening; and the concaved surface permits the first aperture to receive a curved portion of the ring frame.

19. The retractor system of claim 16, wherein:

the segmented body further comprises:
  a third segment comprising a third segment upper surface, a third segment lower surface, a third segment upper jaw, and a third segment side surface coupling the third segment upper surface to the third segment lower surface; and
  a fourth segment comprising a fourth segment upper surface, a fourth segment lower surface, a fourth segment lower jaw, and a fourth segment side surface coupling the fourth segment upper surface to the fourth segment lower surface;

the third segment upper jaw and the fourth segment lower jaw define a second aperture that passes through the third segment side surface and the fourth segment side surface;

the bore further passes through the third segment and the fourth segment;

the adjustment screw further passes through the third segment and the fourth segment via the bore; and rotation of the adjustment screw in the tightening direction causes the third segment and the fourth segment to apply a second clamping force to an outer surface of a retractor arm shaft passing through the second aperture.

* * * * *